United States Patent [19] [11] 4,413,278
Feinbloom [45] Nov. 1, 1983

[54] OPTICAL COUPLING APPARATUS FOR COUPLING AN ARTHOSCOPE TO A CAMERA

[75] Inventor: Richard E. Feinbloom, New York, N.Y.

[73] Assignee: Designs for Vision, Inc., New York, N.Y.

[21] Appl. No.: 308,409

[22] Filed: Oct. 5, 1981

[51] Int. Cl.³ ............................................. H04N 7/18
[52] U.S. Cl. ...................................... 358/93; 358/98; 358/225; 354/62
[58] Field of Search ............... 358/98, 93, 225; 128/4, 128/5, 6, 7, 8, 9; 350/96.15, 96.26; 403/316, 322, 318, DIG. 4; 354/62

[56] References Cited
U.S. PATENT DOCUMENTS 4,305,386 12/1981 Tawara .................................. 354/62
4,369,767 1/1983 Shishido ................................ 354/62

OTHER PUBLICATIONS

George Berci et al., "Miniature Black and White TV Camera for Endoscopy and Other Medical Applications Bio-Medical Engineering", (Apr. 1972).

Primary Examiner—John C. Martin
Assistant Examiner—Edward L. Coles
Attorney, Agent, or Firm—Arthur L. Plevy

[57] ABSTRACT

An optical coupler which comprises a front clamping section for accomodating an arthoscope. The clamping section includes two semicircular arms which are selectively actuated by a push button. Each arm is biased by a spring which forces the arms to contact and grasp the front end of an arthoscope. Coupled to the other side of the clamp is a focusing section which includes a movable lens. The movable lens is contained within a cylinder and is coupled to an outer cylinder which is slideably positioned with respect to the inner cylinder to enable the lens to move to thereby provide a focusing action. The focusing section is coupled to the input of a television camera. The user can then focus the image from the arthoscope as coupled to the clamping section by means of the focusing section to thereby provide a well defined television signal for many different types of television cameras.

10 Claims, 13 Drawing Figures

OPTICAL COUPLING APPARATUS FOR COUPLING AN ARTHOSCOPE TO A CAMERA

BACKGROUND OF INVENTION

This invention relates to optical couplers and more particularly for coupling an arthoscope to a camera such as a television camera.

An arthoscope is a device or instrument which allows the practioner to examine the internal structures of joints. This is necessary in performing diagnosis of various joint ailments or diseases.

In surgical procedures or for teaching students the practioner desires to couple the arthoscope to a television or other camera while conducting an examination or procedure. In this manner the entire procedure can be viewed on a conventional television receiver.

Thus there are presently available a number of relatively small television cameras which are employed in such procedures. These cameras contain a vidicon tube which converts light images into a signal for application to the television receiver.

The television cameras are not constructed uniformly as is known. For example, the vidicon tube or the lens system is never in the same location from camera to camera. Hence a properly focussed camera will operate with an associated arthoscope and another camera will provide an unfocussed picture. The range of focussing of such cameras is limited and this range may not be suitable for operation with various different types of arthoscope. The focal length of the arthoscope from various manufacturers is never the same and the focal length will differ from each manufacturer. In any event, in order to place the image on a television receiver one must have the ability to focus the image prior to application of the same to the television camera.

In regard to the arthoscope, these devices are also supplied by various manufacturers. There are of course prior art devices which serve to accomodate or hold various optical instruments to enable one to utilize a camera or other device together with an associated optical instrument. For example, U.S. Pat. No. 4,143,938 entitled MICROSCOPE APPARATUS WITH TELEVISION FILM CAMERA issued on Mar. 13, 1979 to R. E. Feinbloom and assigned to the assignee herein. This Patent shows an optical coupler which has an input port which receives a beam of light from a microscope or beam splitter. One output is coupled to a television camera while another port is coupled to a film camera. The coupler uses a lens asssembly to provide par focal registration at the associated ports and uses a pivotable mirror to select a given output port. In any event, in that Patent, the coupling is afforded by conventional screw threads which coact with the corresponding ports of the coupler.

It is an object of the present invention to provide an optical coupler for coupling an arthoscope to a television camera in a simple and reliable manner whereby, the arthoscope can be quickly removed from the coupler. The apparatus also allows one to independently focus the image from the arthoscope prior to directing the image to the television camera.

BRIEF DESCRIPTION OF THE PREFERRED EMBODIMENT

An optical coupler apparatus comprises a clamp section comprising a housing having a first large aperture on a first surface and a second smaller coaxial aperture on a second surface with said apertures communicating, a pair of semicircular clamp members located on said housing and positioned about said large aperture and means for selectively moving said clamp members in and out of said large aperture, a focusing section coupled to said housing at said second surface to surround said smaller aperture, said focussing section having a first cylinder for slideably accomodating a lens, said first cylinder having a longitudinal slot on a surface thereof, a second cylinder slideably positioned about said first cylinder and means extending through said slot and coupling said second cylinder to said lense to allow said lens to move to accomodate focussing and means coupled to said focussing section to accomodate a camera.

DETAILED DESCRIPTION OF THE INVENTION

Figure 1:
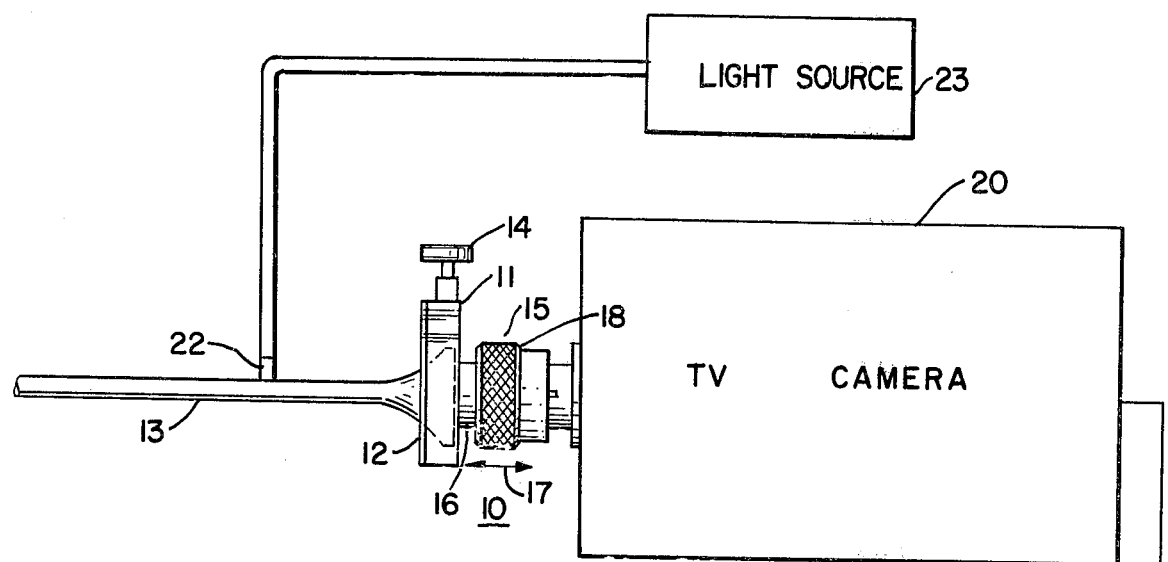
FIG. 1 is a schematic view of an optical coupler employed with an artohscope for use with a television camera.

Referring to FIG. 1, there is shown a typical setup employing the optical coupler 10 according to this invention. As will be explained, the optical coupler 10 includes a clamp section 11. The clamp section has a first opening 12 which will accomodate an arthoscope 13 having a front end of a given diameter and of a varying height. As will be explained, the clamp 11 has an actuating button 14 which enables a pair of semicircular jaws to retract when the button 14 is pressed and upon retraction to release the arthoscope 13.

Coupled to the other side of the clamp section 11 is a lens housing assembly 15. Assembly 15 has a first cylinder 16 which contains a movable lens and which lens can be moved in the direction of arrow 17 to focus the image received from the arthoscope 13 on the target of the vidicon associated with the television camera 20.

As will be explained, a movable locking element 18 allows one to move the lens and hence to provide focusing and thereafter to lock the lens in the optimum position. Associated with the television camera 20 is a television receiver 21. The arthoscope 13 has an inlet port 22 to which is coupled a light source 23. The light source 23 directs a given intensity light beam into the arthoscope to allow the practitioner to illuminate the area as desired. It is of course understood that the arthoscope, the light source, the television camera as well as the receiver are all conventional components and are commercially available.

Figure 2:
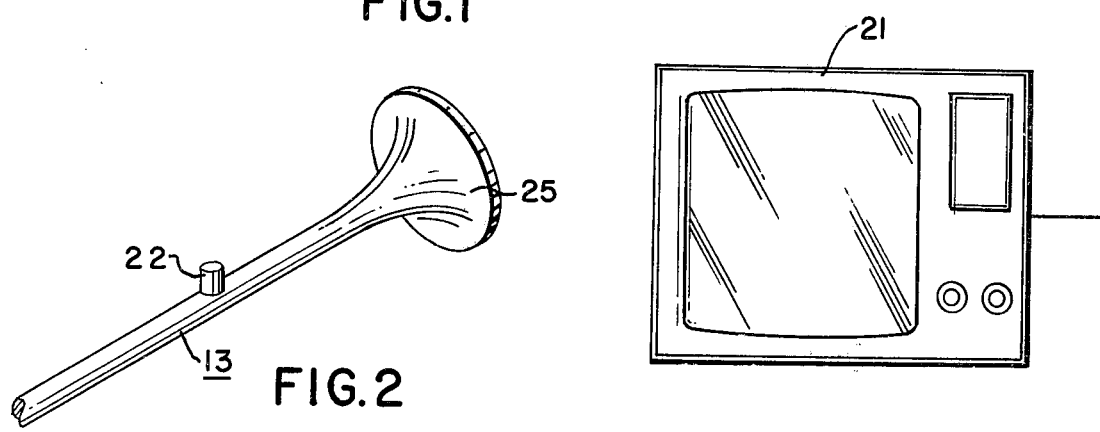
FIG. 2 is a perspective view of an arthoscope.

Referring to FIG. 2, there is shown an arthoscope 13 in a perspective view. Essentially, the arthoscope has a back section 25 of a given diameter as explained. This section allows the physician to look through the instruments or couple to a camera. The coupler 10 also holds the arthoscope 13 via the input section 25 by means of the clamp section 11.

As will be explained, the clamp 11 has two movable arms which grasp and hold the arthoscope about the peripheral edge of the front section 25. The diameter of the front section 25 is relatively equal from instrument to instrument and is the same diameter for arthoscopes manufactured by different companies.

In any event, the thickness of the back end varies and therefore the clamp section 11 has to be able to accomodate the arthoscope having front ends of various thickness.

Referring to FIG. 1, some of the operating advantages of the coupler should be explained. The physician must be able to focus the image from the arthoscope as displayed on the receiver without turning or changing the orientation of the arthoscope and the television camera.

The coupler of this invention allows one to do this. It is also apparent that the arthoscope must be capable of being easily released by the user as desired and the clamp section permits this to be accomplished.

Figures 3A, 3B, 3C:
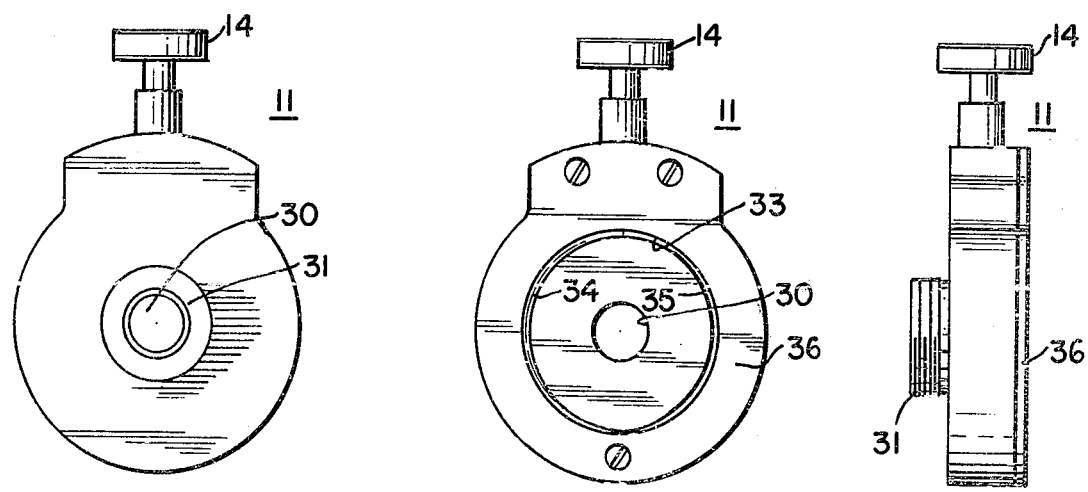
FIGS. 3A to 3C depict a rear, front and side view of a clamping section associated with the coupler.

Referring to FIG. 3A, there is shown a rear view of the clamp section 11 associated with the coupler 10. The clamp section 11 has a central aperture 30 which is surrounded by an extending circular boss 31 as can be more clearly shown in FIG. 3C. The boss 31 is threaded about the periphery to enable the focusing section 15 to be implaced on the clamp section.

FIG. 3B depicts a front view of the clamp section 11. As seen, the front contains a large circular aperture 33 which is of a great enough diameter to accomodate the front section 25 of an arthoscope as 13 of FIGS. 1 and 2. Positioned in the circular opening 33 are two semicircular clamp members 34 and 35 which members are pivoted by means of the push button 14 associated with the clamp section 11.

As will be explained, when button 14 is pushed downwardly and held in that position, the clamp members or arms 34 and 35 are moved out of aperture 33 to thereby allow the practioner to place the back end of an arthoscope within the aperture 33. As button 14 is released, the clamp members which are spring biased will grasp the peripheral edge of the arthoscope back end and hold the same in place. Accordingly, the image from the arthoscope is directed through aperture 30 and thence through the focusing section 15 to the television camera.

Figure 4:
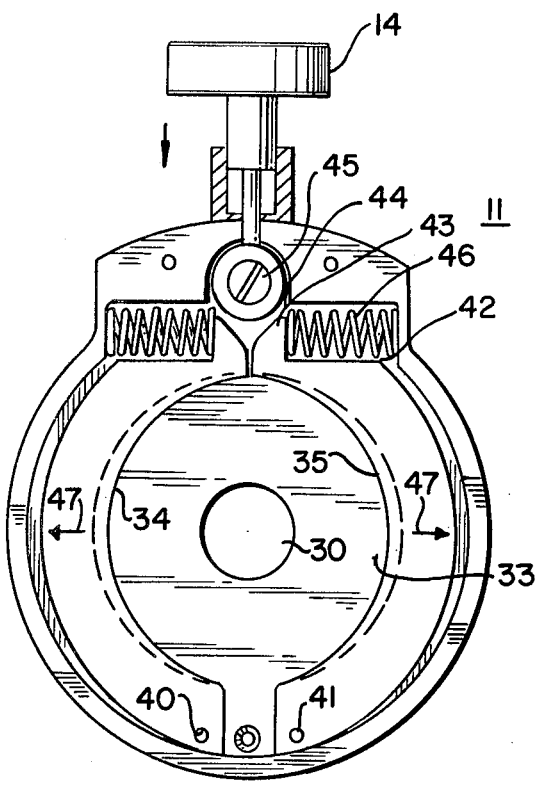
FIG. 4 is a plan view depicting the structure of the clamping section.

Referring to FIG. 4, there is shown the clamp assembly 11 with the front cover 36 removed. Arms 34 and 35 of the clamp section 11 each have a first circular portion and are pivotally mounted within the clamp housing by two pivot pins as 40 and 41 at the lower end of each clamp member.

The inner surfaces of the clamp arms 34 and 35 are "C" or semicircular surfaces as shown. The outer surfaces have an upper top flat area 42 whih is continuous with an extending flange 43. The flange 43 has a sloping front portion 44 for coacting with the circular actuating element 45. Each clamp assembly has a spring which is positioned between the back edge of the flange 43 and the wall of the housing. The spring as 46 is retained within the recess as lying on the top flat surface 42 of each arm 34 and 35. The circular actuating element as seen in FIG. 4 is coupled to the switch 14.

As seen from FIG. 4, when button 14 is pushed downwardly the clamp arms pivot to compress the spring. Each circular arm pivots outwardly or in the direction of arrows 47, for an equal distance. Thus the arms 34 & 35 are removed from blocking the arthoscope aperture 33 as long as the switch 14 is held in the downward position to thus compress the springs 46.

As soon as switch 14 is released, the clamp arms 34 and 35 are forced back into the aperture 33 due to the action of the springs 46. Thus as can be seen the clamp section 11 is extremely simple and reliable and comprises a few parts to provide a reliable and accurate operation.

Figure 5A:
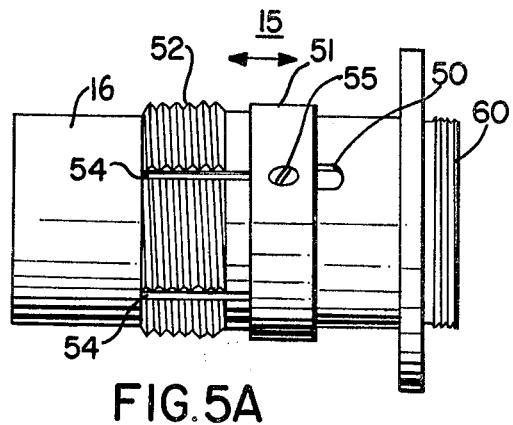
FIGS. 5A to 5C depict side and front views of a focusing section according to this invention.

Referring to FIG. 5A, there is shown a portion of the focusing section 15. Essentially, the focusing section 15 contains an inner housing 16. The housing 16 has two longitudinal slots as 50, one on each side of the cylinder 16. Positioned above cylinder 16 is an outer split cylinder 51. The outer cylinder 51 has a front threaded section 52 and has four channels as 54 located through the threaded section as shown in FIG. 5C.

The cylinder 51 is coupled to an inner housing 56 via set screws or pins 55 which ride in slots 50. The pins 55 as directed through the slot 50 are secured to the lens housing 56 (FIG. 5C). The lens housing 56 contains a lens 57 which enables focusing of the image from the arthoscope as directed to the television camera. The front end of the section 15 contains a threaded section 60 which will engage the input lens of a television camera to allow the coupling element to be secured to the camera.

Figure 5B:
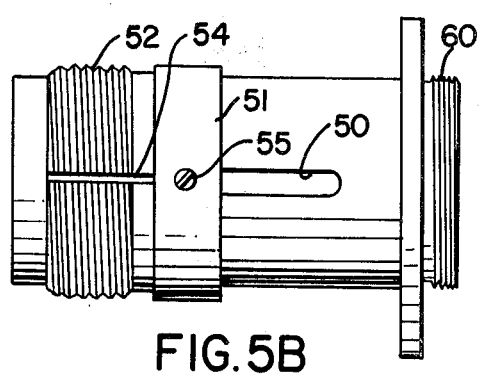
Figure 5C:
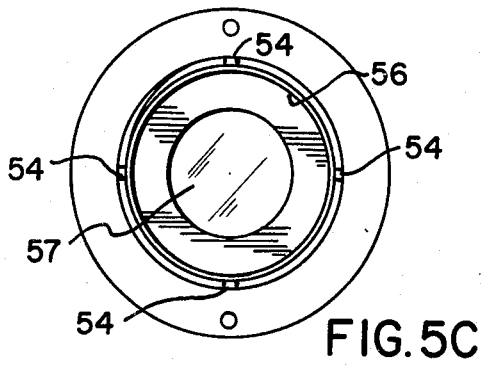

FIG. 5B shows the assembly of FIG. 5A with the outer assembly 51 moved to a front position to depict operation.

Figure 6B:
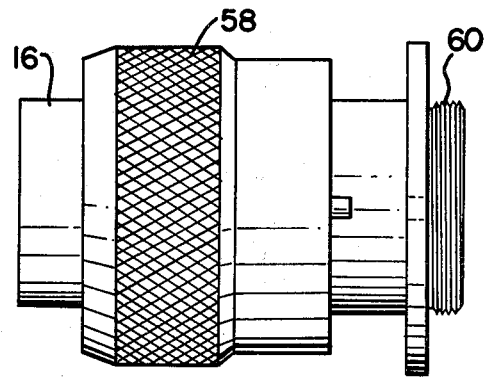
FIG. 6B is a side view of the focusing member coupled to the focusing assembly.
Figure 6A:
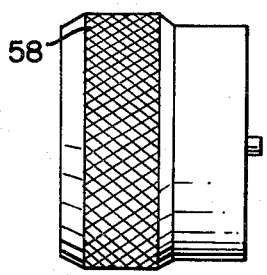
FIG. 6A is a side elevational view of a locking and focusing member.

Referring to FIG. 6A, there is shown a side view of a locking and adjustment nut 58 which corresponds to member 18 of FIG. 1.

As shown in FIG. 6B, the member 58 is secured to member 51 via the threaded section 52.

Figure 6C:
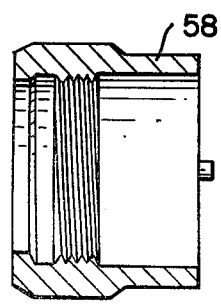
FIG. 6C is a sectional view of the member shown in FIG. 6A.

As seen in FIG. 6C, the inner surface of members 58 is also threaded. As member 58 is rotated, the front portion of member 58 will engage the threaded portion 52 of member 51 exert a compressing force on the front threads 52 which force will lock the lens in any position as determined by the slot 50. When member 58 is turned in the opposite direction, it allows the member 51 to slide on cylinder 16 to allow the user to focus the entire assembly.

Figure 7:
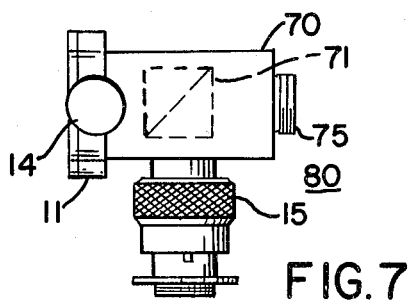
FIG. 7 is a top plan view of a right angled optical coupler according to this invention.

Referring to FIG. 7, there is shown an optical coupler device 80 which employs a clamp section 11 and a focusing section 15 as does the coupler 10 of FIG. 1 but which employs an additional coupling block 70. Block 70 contains a prism or beam splitter 71. In this coupler the image which emanates from the arthoscope as held by the clamp 11 is bent 90° via the prism 71 to enter the section 15 which is coupled to the television camera. The bend of 90° allows that practioner more versatility in regard to performing certain procedures. In place of a prism one could use a beam splitter and therefore a beam of light would be directed to the focusing section 15 as bent by 90° and a beam would also be directed to port 75 and therefore another camera such as a film camera and so on could be coupled to port 75.

The above described coupler is relatively simple to make and operates reliably in that few parts are employed. The coupler allows one to independently focus the image sent to a television camera to enable the arthoscope to be used with various television cameras as manufactured by different companies. The entire unit is simple to fabricate and construct.

I claim:

1. An optical coupler apparatus comprising:
a clamp section comprising a housing having a first large aperture on a first surface and second smaller coaxial aperture on a second surface with said apertures communicating, a pair of semicircular clamp members located on said housing and positioned about said large aperture and means for selectively moving said clamp members in and out of said large aperture,
a focusing section coupled to said housing at said second surface to surround said smaller aperture, said focusing section having a first cylinder for slideably accomodating a lens, said first cylinder having a slot on a surface thereof, a second cylinder moveably positioned about said first cylinder and through said slot coupling said second cylinder to said lens to allow said lens to move to accomodate focusing and means coupled to said focusing section to accomodate a camera.

2. The optical coupler apparatus according to claim 1 wherein said semicircular clamp members each have a central "C" shaped section facing each other, pivot means coupled to the bottom end of said "C" section to enable said members to pivot about said bottom end, with the top end of each "C" section having an upwardly extending flange and activator means coupled to coact with said flange to pivot said members.

3. The optical coupler apparatus according to claim 2 further including a first and a second spring, said first spring coupled to said extending flange of said first clamp member and said second spring coupled to the extending flange of said second clamp member.

4. The optical coupler apparatus according to claim 1 wherein said large aperture is dimensioned to accomodate the front end of an arthoscope.

5. The optical coupler apparatus according to claim 1 wherein said camera coupled to said focusing section is a television camera.

6. The optical coupler apparatus according to claim 1 wherein said second cylinder has a first section which is threaded and a plurality of grooves located about the surface of said second cylinder.

7. The optical coupler apparatus according to claim 6 further including a locking cylinder having an inner threaded surface and adapted to be positioned over said second cylinder to engage the threads of said second cylinder and to compress said channels to lock said second cylinder in position with respect to said first cylinder manifesting a desired focus position.

8. The optical coupler apparatus according to claim 1 further including means located between said clamp section and focusing section for bending a light beam at an angle of 90°.

9. The optical coupler apparatus according to claim 8 wherein said means is a beam splitter.

10. The optical coupler apparatus according to claim 8 wherein said means is a prism.

* * * * *